United States Patent [19]
Aruffo et al.

[11] Patent Number: 5,861,151
[45] Date of Patent: Jan. 19, 1999

[54] SOLUBLE FUSION MOLECULES WITH BINDING SPECIFICITY FOR CELL ADHESION MOLECULES

[75] Inventors: Alejandro A. Aruffo, Edmonds; Nitin Damle, Renton, both of Wash.

[73] Assignee: Bristol-Myers Squibb Co, Princeton, N.J.

[21] Appl. No.: 811,129

[22] Filed: Dec. 20, 1991

[51] Int. Cl.⁶ .................. C07K 19/00; A61K 31/395; A61K 45/00
[52] U.S. Cl. .................. 424/134.1; 424/136.1; 424/130.1; 435/69.7; 530/350; 530/387.3
[58] Field of Search .................. 530/387, 350, 530/388.75, 387.3; 536/27; 435/69.7; 424/134.1, 130.1, 136.1

[56] References Cited

PUBLICATIONS

Springer Nature 346:425–434 1990.
Zettlmeissl et al, DNA & Cell Biology 9:347–353 '90.
Staunton, et al Nature 339:61–64 1987.
Altmann et al. (1989) Nature 338:512–514.
Aruffo et al. (1990) Cell 61:1303–1313.
Bierer et al. (1988) J. Exp. Med. 168:1145–1156.
Boyd et al. (1988) Proc. Natl. Acad. Sci. USA 85:3095–3099.
Clevers et al. (1988) Ann. Rev. Immunol. 6:629–662.
DeFougerolles et al. (1991) J. Exp. Med. 174:253–267.
Dustin et al. (1986) J. Immunol. 137:245–254.
Kishimoto et al. (1989) "The Leukocyte Integrins" In Advances In Immunology 46:149–182.
Linsley et al. (1991) J. Exp. Med. 173:721–730.
Makgoba et al. (1988) Nature 331:86–88.
Marlin et al. (1987) Cell 51:813–819.
Moingoen et al. (1989) 339:312–314.
Newman et al. (1990) Science 247:1219–1222.
Nortamo et al. (1991) J. Immunol. 146:2530–2535.
Simmons et al. (1988) Nature 331:624–627.
Simmons et al. (1990) J. Exp. Med. 171:2147–2152.
Staunton et al. (1988) Cell 52:925–933.
Staunton et al. (1990) Cell 62:243–254.
Van Seventer et al. (1990) J. Immunol. 144:4579–4586.

*Primary Examiner*—Frank C. Eisenschenk
*Attorney, Agent, or Firm*—Joseph M. Sorrentino

[57] ABSTRACT

Soluble fusion molecules were prepared which contained a CD11a/CD18 specific binding region operatively linked to an immunoglobulin constant region. These molecules particularly include extracellular portions of adhesion molecules such as ICAM-1 and ICAM-2 attached to IgG constant regions.

The fusion molecules described are utilized as costimulatory agents for the activation of T cells and in methods for increasing CD4⁺ T cell proliferative response and IL-2 induction.

17 Claims, 8 Drawing Sheets

SOLUBLE FUSION MOLECULES WITH BINDING SPECIFICITY FOR CELL ADHESION MOLECULES

TECHNICAL FIELD OF THE INVENTION

The present invention is directed to soluble fusion molecules that possess a region having a binding specificity for CD11a/CD18 and a region corresponding to an immunoglobulin constant region, such as a recombinant molecule containing an extracellular CD11a/Cd18 binding region of ICAM-2 and a constant region of an IgG. The molecules of the present invention are further utilized in methods to affect T cell responses and activity.

BACKGROUND OF THE INVENTION

The CD3/TCR (T cell antigen receptor) complex on the surface of T cells not only recognizes nonself antigen (Ag) in the context of self major histocompatibility (MHC) molecules expressed on the surface of antigen presenting cells (APC) but also participates in signal transduction to initiate the activation of T cells (Clevers H. et al. (1988) Ann. Rev. Immuno. 6: 629). The interaction between CD3/TCR and Ag/MHC on APC, although essential to initiate the activation of T cells, is usually not sufficient and requires participation of additional cell-surface molecules which mediate adhesion and/or signal transduction for optimal expression of various functions of activated T cells (Clevers H. et al. (1988) Ann. Rev. Immuno. 6: 629; Springer T. A. (1990) Nature 346: 425; Moller G. (1990) Immunol. Rev. 114: 1–217).

The leukocyte adhesion molecule LFA-1 (CD11a/CD18) expressed on the surface of all mature leukocytes mediates a wide range of interactions with other somatic cells during the immune response and inflammation by interaction with its ligand the intercellular adhesion molecule-1 (ICAM-1/CD54) (Springer T. A. (1990) Nature 346: 425; Moller G. (1990); Moller G. (1990) Immunol. Rev. 114: 217; Kishimoto T. K. et al. (1989) Adv. Immunol. 46: 149; Marlin S. D. et al. (1987) Cell 51: 813; Makgoba M. W. et al. (1988) Nature 331: 86; Staunton D. E. et al. (1988) Cell 52: 925; Simmons, D. et al. (1988) Nature 331: 624; Staunton D. E. et al. (1990) Cell 61: 243; Boyd A. W. et al. (1988) Proc. Natl. Acad. Sci. USA 85: 3095; Dougherty, G. et al. (1988) Eur. J. Immunol. 18: 35; Altmann D. M. et al. (1989) Nature 338: 512). ICAM-1 is constitutively expressed on some tissues and induced on others during inflammation (Dustin M. L. et al. (1986) J. Immunol. 137: 245). ICAM-1 provides an important costimulatory signal via its adhesive interaction with LFA-1 during the CD3/TCR-mediated activation of resting T cells (Van Seventer G. A. et al. (1990) J. Immunol. 144: 4579). Recently, another ligand for LFA-1, ICAM-2 has been identified which can mediate the ICAM-1 independent adhesion of LFA-1$^+$ cells (Staunton D. E. et al. (1989) Nature 339: 61; Dustin M. L. et al. (1989) Cold Spring Harbor Symp. Quant. Biol. 54: 753). Expression of ICAM-2 is restricted and is not readily upregulated with proinflammatory stimuli (De Fougerolles A. R. et al. (1991) J. Exp. Med. 174: 253; Nortamo, P. et al. (1991) J. Immunol. 146: 2530).

In the present invention soluble recombinant ICAM-1 and ICAM-2 immunoglobulin fusion proteins have been created to analyze and compare the roles of these molecules in cellular interactions underlying various immune responses. This invention shows that, like its homologue ICAM-1, ICAM-2 can provided an imporant costimulatory signal during the TCR-mediated activation of CD4$^+$ cells. The costimulatory signal during the TCR-mediated activation of CD4$^+$ T cells. The costimulatory adhesion mediated by LFA-1:ICAM-2 interaction may provide a critical pathway for the initiation of T cell activation with ICAM-1$^-$ or ICAM-1$^{low}$ICAM-2$^+$ APC.

SUMMARY OF THE INVENTION

The present invention is directed to soluble fusion molecules and methods of use. These fusion molecules contain a region that possesses a binding specificity for CD11a/CD18. This region is operatively linked, or joined, to a second region which substantially corresponds to an immunoglobulin constant region. Several adhesion molecules are known which have a binding specificity for CD11a/CD18. Most of these molecules are cell-membrane associated and thus insoluble, and include ICAM-1, and ICAM-2.

In this invention the soluble, extracellular portion of such an adhesion molecule that retains binding specificity for CD11a/CD18 is utilized. This extracellular region is linked to an Ig constant region such as an IgG or IgM constant region. One example of a fusion molecule of this invention is a protein having one region that substantially corresponds to an extracellular portion of ICAM-2 and an second region that substantially corresponds to a portion of an IgG constant region. The molecules of this invention can be produced by either chemical synthesis or recombinant expression.

When a recombinant fusion molecule is utilized, it can be produced by standard techniques of gene cloning. For example, a specific recombinant fusion molecule of ICAM-2 and IgG constant region can be produced by first subcloning a cDNA encoding an extracellular portion of ICAM-2 into an IgG expression vector. The cloned DNA can then be transcribed and the fusion molecule expressed. The expressed protein is then isolated yielding a recombinant fusion molecule containing an extracellular portion of ICAM-2 operatively linked to an IgG constant region.

The fusion molecules of the present invention can be utilized as costimulatory agents for the activation of T cells and in methods for increasing the proliferative response of CD4$^+$ T cells and the induction of IL-2 by T cells. T cells can be activated by a method of the present invention by contacting the cells with a ligand capable of binding CD3 on the T cells and an effective costimulatory amount of a fusion molecule of this invention. T cell proliferation and IL-2 induction is stimulated in the present invention by contacting susceptible T cells with a fusion molecule of this invention for a time period sufficient to induce cell growth and IL-2 induction, respectively.

DESCRIPTION OF PREFERRED EMBODIMENTS

Figure 1:
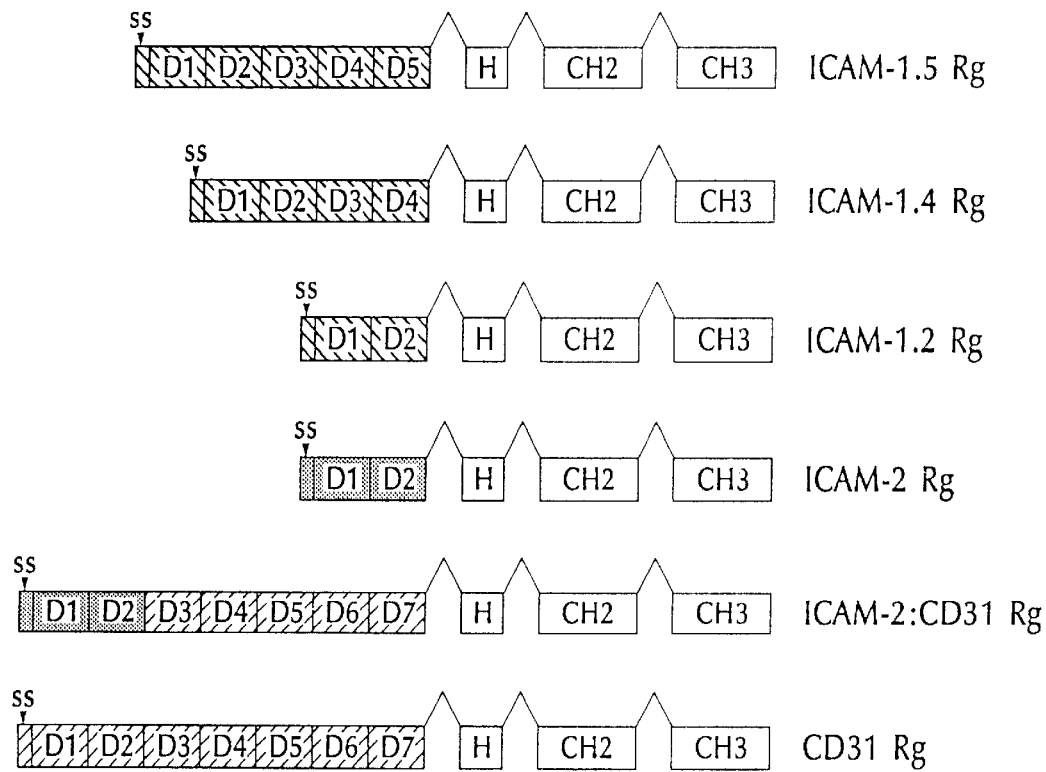
FIG. 1 illustrates soluble ICAM Rg fusion genes. Antibody exons (human IgG1) are denoted by black boxes and introns by connecting lines. H, CH2 and CH3 denote the IgG1 hinge, CH2 and CH3 constant region exons, respectively, ICAM-1 N-terminal signal sequence (SS) and Ig-like domains (D1–D5) are shown as stippled boxes. ICAM-2 N-terminal SS and Ig-like domains (D1 and D2) are shown in striped boxes. CD31 N-terminal SS and Ig-like (D1–D7) domains are denoted as white boxes.

Activation of T cells often requires both signals delivered by ligation of the TCR and those resulting from costimulatory interactions between certain T cell surface accessory molecules and their respective ligands on APC. LFA-1 on T cells modulate the activation of T cells by interacting with its ligands ICAM-1 and/or ICAM-2 on the surface of APC. The costimulatory ability of ICAM-1 has been demonstrated. Here, a soluble ICAM-2 immunoglobulin fusion protein (receptor globulin, Rg) is used to demonstrate the costimulatory effect of ICAM-2 during the activation of CD4+ T cells. When co-immobilized with anti-TCR-1 mAb, ICAM-2 Rg induced vigorous proliferative response of CD4+ T cells. This costimulatory effect of ICAM-2 was dependent on its co-immobilization with mAb directed at the CD3/TCR complex but not those directed at CD2 or CD28. Both resting as well as antigen-primed CD4+ T cells responded to the costimulatory effects of ICAM-2. The addition of mAb directed at the CD11a or CD18 molecules almost completely inhibited the responses to ICAM-2 Rg. These results are consistent with the role of the LFA-1 complex as a receptor for, and mediator of, ICAM-2 costimulatory effects. Stimulation of T cells with co-immobilized anti-TCR-1 and ICAM-2 resulted in the induction of IL-2 receptor (CD25), and anti-Tac (CD25) mAb inhibited this response suggesting the contribution of endogenously synthesized IL-2 during this stimulation. These results demonstrate that like its homologue ICAM-1, ICAM-2 also exerts a strong costimulatory effect during the TCR-mediated activation of T cells. The costimulatory effects generated by the LFA-1:ICAM-2 interaction may be critical during the initiation of T cell activation by ICAM-$1^{low}$ APC.

In order to more clearly describe the present invention and its embodiments, the following definitions are included.

"Transfection", as used herein, is the acquisition of new genetic markers by incorporation of added DNA into eukaryotic cells.

"Transformation", as used herein, is the acquisition of new genetic markers by incorporation of added DNA into prokaryotic cells.

"Cloning vector", as used herein, is any plasmid or virus into which a foreign DNA may be inserted to be cloned.

"Plasmid", as used herein, is an autonomous self-replicating extra-chromosomal circular DNA.

"Open Reading Frame" (ORF), as used herein, is a DNA sequence which is (potentially) translatable into protein.

"Gene (cistron)", as used herein, is the segment of DNA that encodes the sequence of a peptide chain; it can include regions preceding and following the coding region (leader and trailer) as well as intervening sequences (introns) between individual coding segments (exons).

"Expression", as used herein, is the process undergone by a structural gene to produce a peptide or protein. It is a combination of transcription and translation.

As used herein, the term "clone" describes any number of identical cells or molecules with a single ancestral cell or molecule.

As used herein, the term "base pair" (bp) is a partnership of adenine (A) with thymine (T), or of cytosine (C) with guanine (G) in a DNA double helix.

As used herein, the term "expression vector" is any plasmid or virus into which a foreign DNA may be inserted and/or expressed. Illustrative expression vectors include those expressing the CD8-IgG1 protein (Aruffo et al. (1990) Cell 61: 1303–1313) and the CD4-IgG1 and CD4-IgM proteins (Zattlmeissl et al. (1990) DNA Cell Biol. 9: 347–353).

As used herein, the term "polymerase chain reaction" (PCR) refers to the amplification of DNA molecules by the successive use of a temperature stable DNA polymerase to copy the DNA chain, separating the complementary chains by heating, adding primers and repeating the process about 30 times to produce approximately $10^9$ copies of the DNA. By use of the PCR technique, minute amounts of DNA can be amplified to produce sufficient DNA for use in various procedures.

The term "synthetic" as used herein refers to a peptide molecule that has been built up by chemical means, that is, chemically synthesized, rather than being prepared by a biological means such as by genetic engineering techniques.

As used herein the term "effective amount" means an amount sufficient to beneficially produce the desired result.

The term "correspond" in its various grammatical forms, as used herein and in the claims in relation to peptide or protein sequences means the sequence described plus or minus up to ten amino acid residues at either or both of the amino and carboxy termini and containing only conservative substitutions in particular amino acid residues along the peptide and/or protein sequence.

The term "conservative substitution" as used above denotes that one amino acid residue has been replaced by another, biologically similar residue. Examples of conservative substitutions include the substitutions of one hydrophobic residue such as Ile, Val, Leu, or Met for another, or the substitution of one polar residue for another such as between Arg and Lys, between Glu and Asp or between Gln and Asn, and the like.

In some instances the replacement of an ionic residue by an oppositely charged ionic residue such as Asp by Lys has been determined conservative in the art in that those ionic groups are thought to merely provide solubility assistance. In general, however, since the replacements discussed herein are on a relatively short synthetic peptide region, as compared to a whole protein, replacement of an ionic residue by another ionic residue of opposite charge is considered herein to be a "radical replacement" as are replacements by nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that either bear no charge or normally bear a charge, respectively, at physiological pH value. Exemplary nonionic residues include Thr and Gln, while exemplary ionic residues include Arg and Asp.

As used herein, the term "cellular adhesion molecule" refers to specific inflammatory cell surface molecules that are recognized by and bind to vascular endothelium and/or granulocytes.

As used herein, the term "IgG constant region" refers to domains of the gamma chain of the IgG molecule that are adjacent to the variable region that corresponds to the first 107 amino acids of the gamma chain or fragments thereof. The four domains within the gamma chain constant region are designated $CH_1$, H, $CH_2$, and $CH_3$. $CH_1$ is adjacent to the variable region and encompasses amino acid residues 114 through 223. H (hinge; residues 224–245) is adjacent to $CH_1$ and contains the cysteine residues that form the disulfide bonds which covalently link the two immunoglobulin heavy chains. $CH_2$ is adjacent to the hinge and encompasses amino acid residues 246 through 361, followed by $CH_3$ which contains amino acid residues 362 through 496.

As used herein, the term "library" refers to a large random collection of cloned DNA fragments obtained from the transcription system of interest.

As used herein the term "operatively linked" refers to a linkage that does not interfere with the ability of either of the linked groups to function as described. Such linkages can be formed by synthetic and/or recombinant means. In one preferred embodiment, an ICAM-2 extracellular region is operatively linked to a constant portion of an immunoglobulin molecule such as an IgG constant region in a manner that permits the ICAM-2 region to bind to a CD11a/CD 18.

As used herein, the term "pharmaceutically acceptable carrier" refers to a compound which is compatible with administration to a patient and does not produce toxic or untoward effects upon such administration. Illustrative examples of pharmaceutically acceptable carriers are phosphate buffered saline, Ringer's solution, oils, gels and microspheres, as well as liposomes. Other pharmaceutically acceptable carriers are well known in the field of pharmacy and are contemplated by the present invention.

As used herein the term "substantially" refers to a high level of similarity. A substantially purified peptide of the present invention refers to a preparation having less than about ten percent extraneous peptides present. A substantially similar sequence in the present invention has less than about ten percent variation with the reference sequence.

As used herein the term "cloning" and its grammatical forms refers to the insertion of DNA sequence into the genome of a prokaryotic or eukaryotic cell or organism wherein it can be reproduce identically. Such cloning results in the production of recombinant DNA molecules formed by the end to end joining of different DNAs.

As used herein the term "subcloning" and its various grammatical forms refers to the insertion of a genomic fragment cDNA sequence into an expression vector.

As used herein the term "region" as it relates to a molecule refers to any designated or described portion or domain of the molecule such as an extracellular portion or region of an adhesion molecule such as ICAM-1 or ICAM-2 or an IgG constant region.

As used herein, the term "fusion molecule" refers to a constructed molecule that contains designated regions and/or characteristics of two or more different molecules. In the present invention the fusion molecules contain a region of an adhesion molecule and a region of an immunoglobulin. In the present invention this results in a soluble fusion molecule that possesses the binding specificity of a cellular adhesion molecule. Fusion molecules can be prepared by either synthetic or recombinant methods.

As used herein, the term "binding specificity" refers to the selective affinity of one molecule for another such as the binding of antibodies to antigens, receptors to ligands, and enzymes to substrates. All molecules that bind to a particular entity are deemed to have binding specificity for that entity. Thus all antibodies that bind a particular antigen have binding specificity for that antigen, and all ligands that bind to a specific cellular receptor have binding specificity for that receptor.

The present invention is directed to novel soluble fusion molecules and methods which, in a preferred embodiment, demonstrate that ICAM-2, like its homologue ICAM-1, can function as a costimulatory counter-receptor/ligand during the activation of T cells. This observation allows ICAM-2 to be included into a subgroup of Ig supergene family members capable of functioning as costimulatory molecules. This subgroup includes B7, ICAM-1, LFA-3, and VCAM-1 (Van Seventer G. A. et al. (1990) J. Immunol. 144: 4579; Damle N. K. et al. (1991) Proc. Natl. Acad. Sci. USA 88: 6403; Bierer B. E. et al. (J. Exp. Med. 168: 1145; Moingeion P. et al. (1989) Nature 339: 312; Linsley P. S. et al. (1991) J. Exp. Med. 173: 721). All of these molecules, and others known to those skilled in the art may be utilized to form fusion molecules in the present invention. Costimulations with ICAM-2 was shown to be absolutely dependent on the costimulations of T cells via the CD3/TCR complex and required that both anti-TCR-1 and ICAM-2 be co-immobilized on the same surface. The costimulatory effect of ICAM-2 was strikingly similar to that of ICAM-1, perhaps due to the fact that both ICAM-1 and ICAM-2 share the same surface receptor, the LFA-1 (CD11a/CD18) molecule (Marlin S. D. et al. (1987) Cell 51: 813; Mkgoba M. W. et al. (1988) Nature 331: 86; Stauton D. E. et al. (1989) Nature 339: 61; Dustin M. L. et al. (1989) Cold Spring Harbor Symp. Quant. Biol. 54: 753).

In spite of the use of the same receptor (LFA-1), the responses induced by ICAM-1 and ICAM-2, although kinetically similar, were quantitatively different. The proliferative responses induced with ICAM-2 were also reflected in their respective abilities to induce the expression of surface IL-2R and synthesize IL-2. The observed stronger costimulatory effects of ICAM-1 compared to those of ICAM-2 may have been due to differences in the relative avidities of the interaction of these two molecules with LFA-1; ICAM-1 having stronger avidity for LFA-1 than ICAM-2 (Staunton D. E. et al. (1989) Nature 339: 61; Dustin M. L. et al. (1989) Cold Spring Harbor Symp. Quant. 54: 753; De Fougerolles A. R. et al. (1991) J. Exp. Med. 174: 253). The extracellular domain of ICAM-1 is composed of five Ig-like domains whereas the extracellular domain of ICAM-2 possesses only two such domains (Staunton D. E. et al. (1988) Cell 52: 925, Simmons D. et al. (1988) Nature 331: 624, Staunton D. E. et al. (1989) nature 339: 61). Inhibition studies with distinct anti-ICAM-1 mAb have mapped the LFA-1 interaction site on ICAM-1 to the first domain of the ICAM-1 molecule (D1 in FIG. 1) with some contribution from domain 2 (Staunton D. E. et al. (1990) Cell 61: 243). Although the two most N-terminal domains of ICAM-1 and ICAM-2 which contribute to their interactions with LFA-1 show 34% identity (Staunton D. E. et al. (1989) Nature 339: 61), the presence of 3 additional domains in the ICAM-1 molecule may in part provide additional flexibility to the binding domains of ICAM-1 (D1 and D2) and thus account for its stronger avidity for LFA-1.

Figure 4:
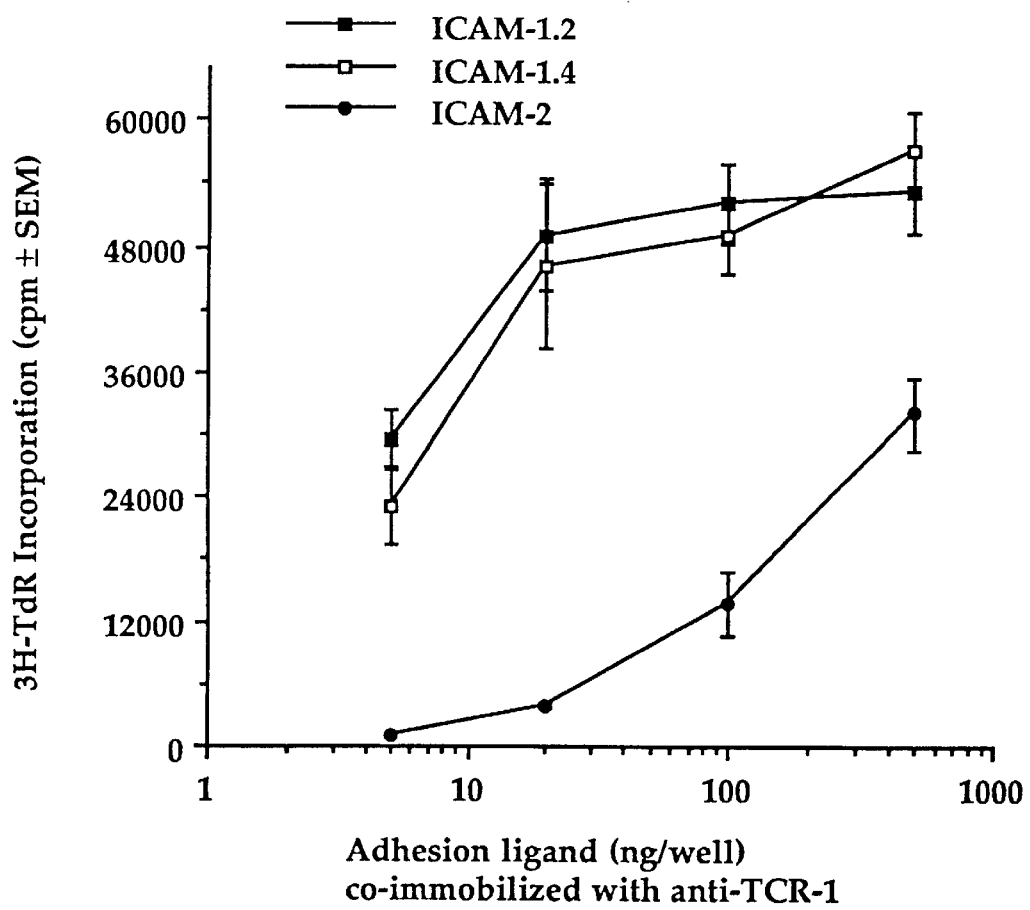
FIG. 4 illustrates the concentration dependence of the costimulatory effects of ICAM-1 and ICAM-2 Rgs. ICAM-1.2, ICAM-1.4, or ICAM-2 Rgs at various concentrations were co-immobilized with anti-TCR-1 mAb (50 ng/well) prior to the addition of fifty thousand resting CD4+ T cells/well. Proliferative responses in these cultures were measured on day 4.

The possibility that the presence of additional domains in the structure of ICAM-1 makes it a stronger costimulatory molecule than ICAM-2 was addressed experimentally by genetically engineering an ICAM-1 Rg molecule which possessed only the two most N-terminal domains of ICAM-1, ICAM-1.2 Rg. When directly compared, ICAM-1.2 Rg was still stronger in its costimulatory effect than ICAM-2 Rg (FIG. 4). These data are consistent with, and further support, the conclusion that the two most N-terminal Ig-like domains of ICAM-1 are critical in its interactions with LFA-1 (Staunton, D. E. et al. (1988) Cell 52: 925, Staunton D. E. et al. (1990) Cell 61: 243).

The size of the ICAM-2 molecule was increased by providing it with five additional Ig-like domains from the CD13 molecule. The ICAM-2: CD31 Rg chimera, which contains the extracellular domain of ICAM-2 replacing the two most N-terminal of the seven Ig-like domains of CD31 (Newman P. J. et al. (1990) Science 247: 1219; Simmons D. L. et al. (1990) J. Exp. Med. 171: 2147), was no more or less efficient at costimulating T cells than the ICAM-2 Rg molecule. Collectively, these results indicate that the in vitro differences in the costimulatory effects of ICAM-1 and ICAM-2 may originate from the differences in the primary structures of the two most N-terminal Ig-like domains of the respective molecules and not from differences in the length and/or flexibility of the two molecules. Although the purified ICAM-1 Rgs with different domains were found to be equally costimulatory (data not shown), the presence of additional domains in the native ICAM-1 molecule may project it further in the extracellular space thereby reducing interference by the cellular glycocalyx (Staunton D. E. (1989) Nature 339: 61; De Fougerolles A. R. et al. (1991) J. Exp. Med. 174: 253). The ICAM-2 molecule in its native form may not possess this advantage, and perhaps for this reason, in a physiological context ICAM-2 mediated adhesion is weaker than ICAM-1 mediated adhesion (Staunton D. E. (1989) Nature 339: 61; De Fougerolles A. R. et al. (1991) J. Exp. Med. 174: 253).

The costimulatory effect of the interaction between ICAM-1 and LFA-1 on T cells has been observed in Ag-stimulated as well as anti-CD3 stimulated systems (Altmann D. M. et al. (1989) Nature 338: 512; Van Seventer G. A. et al. (1990) J. Immunol. 144: 4579). The present invention shows that the costimulatory effects of ICAM-2, although dependent on the interaction between ICAM-2 and LFA-1, are also CD3/TCR dependent. LFA-1 on resting T cells does not bind to immobilized ICAM-1 (Van Seventer G. A. et al. (1990) J. Immunol. 144: 457; Dustin M. L. et al. (1989) Nature 341: 619) or ICAM-2. Agonists of PKC such as PMA, which increase the avidity of LFA-1 for ICAM-1 (Van Seventer G. A. et al. (1990) J. Immunol. 144: 457; Dustin M. L. et al. (1989) Nature 341: 619) do not induce ICAM-1 or ICAM-2 dependent proliferation of T cells. However, ligation of the CD3/TCR complex on T cells which causes both the activation of PKC as well as mobilization of intracellular free $Ca^{2+}$ (Weiss, A. et al. (1986) Annu. Rev. Immunol. 4: 593) not only increases the avidity of LFA-1 for ICAMS (Van Seventer G. A. et al. (1990) J. Immunol. 144: 457; Dustin M. L. et al. (1989) Nature 341: 619) but also enables T cells to receive costimulatory signals delivered by ICAMs (Van Seventer G. A. et al. (1990) J. Immunol. 144: 457). Although the molecular mechanisms by which ligands of LFA-1 deliver their activation signals remain poorly understood, cross-linking with mAb directed at CD3/TCR and LFA-1 induces much more prolonged mobilization of intracellular free $Ca^{2+}$ and hydrolysis of phosphatidyl inositol than that with anti-CD3 mAb alone (Wacholtz, M. C. et al. (1989) J. Exp. Med. 170: 431; Pardi R. et al. (1989) J. Immunol. 143: 3157). Although not directly examined here, ICAMs when immobilized with anti-TCR-1 may induce similar prolonged generation of second messengers which is essential for T cell activation. Upon activation, CD18 (LFA-1β) is rapidly phosphorylated at serine whereas constitutive serine-phosphorylation of CD11a remains unchanged (Catila T. A. et al. (1988) J. Immunol. 140: 4308). More importantly, upon activation of T cells with Ag-pulsed APC the LFA-1 complex co-localizes with the CD3/TCR at the focal point of contact between T cells and APC accompanied by the reorganization of the cytoskeleton perhaps via physically engaging cytoskeletal component talin (Kupfer A. et al. (1989) Annu. Rev. Immunol. 7: 309). If so, it would be of interest to examine if the difference in the costimulatory effects of ICAM-1 and ICAM-2 is actually due to the differential engagement by ICAMs via LFA-1 of cytoskeletel elements (Kupfer A. et al. (1989) Annu. Rev. Immunol. 7: 309) to redirect the activation processes (Van Noesel, C. et al. (1988) Nature 330: 850).

Unlike that of ICAM-1, the expression of ICAM-2 appears to be much more restricted and not modulated by inflammatory cytokines (Staunton D. E. et al. (1989) Nature 339: 61; Nortamo P. et al. (1991) J. Immunol. 146: 2530). ICAM-2 is present predominantly on vascular endothelial cells and certain interstitial cells including dendritic cells (Staunton D. E. et al. (1989) Nature 339: 61; De Fougerolles A. R. et al. (1991) J. Exp. Med. 174: 253; Nortamo P. et al. (1991) J. Immunol. 146: 2530). In light of its costimulatory effect, ICAM-2 may support the activation of T cells by ICAM-1 or $^{low}$APC before the expression of ICAM-1 can be upregulated. Given the stronger expression of ICAM-2 on vascular endothelial cells the costimulatory behavior of ICAM-2 may be of significance during the pathogenesis of certain inflammatory responses. For example, ICAM-2 expressed on vascular endothelial cells may support adhesion/activation of intravascularly activated T cells to initiate and subsequently exacerbate the intravascular inflammatory manifestations associated with toxic shock syndrome induced by staphylococcal exotoxins (Super Ag) or vascular shock syndrome associated with the administration of high doses of IL-2 during cancer therapy (Resnick S. D. (1990) J. Pediatr. 116: 321; Damle N. K. et al. (1989) J. Immunol. 142: 2660). Thus, any therapeutic modalities directed at inhibiting the ICAM-2 dependent interactions may prove to be clinically advantageous for the treatments of intravascular inflammatory diseases.

Having generally described this invention, a further understanding can be obtained by reference to certain specific examples which are provided herein for purposes of illustration only and are not intended to be limiting unless otherwise specified.

EXAMPLE 1

Construction and Preparation of the ICAM Rg

ICAM-1 cDNA sequences encoding the most N-terminal 2 or 4 Ig-like domains or the complex extracellular domain of ICAM-1 were amplified by polymerase chain reaction (PCR) with synthetic oligonucleotides complementary to sequences flanking this region from 1 ng of a cDNA encoding the ICAM-1 molecule (Simmons D. et al. (1988) Nature 331: 624) as a template by 25 cycles of PCR. Each cycle consisting of 30 sec. at 92 C.°, 2 min. at 55 C.° using the reaction buffer recommended by the enzyme vendor (United States Biochemical). Oligonucleotides were designed to allow the creation of restriction enzyme cleavage sites at the 5' and 3' extremities of the amplified cDNA segments to facilitate subsequent insertion into the IgG1 expression vector (Damle N. K. et al. (1991) Proc. Natl. Acad. Sci. USA 88: 6403). For these three constructions, a forward primer encoding sequences located in the expression vector containing a full length cDNA clone encoding the ICAM-1 protein was synthesized with the following sequences:

5'GTA CGG GCC AGA TAT ACG CGT TGA CAT TGA TTA-3'.

Reverse primers encoding sequences located at the junction of the 2nd and 3rd Ig-like domains, the 4th and 5th Ig-like domains, and at the end of the 5th Ig-like domain containing a BAMHI with the following sequences were synthesized:

5'CCT AGG ATC CGG GGG AGT CGC TGG CAG GAC AAA GGT-3';

5-CCT AGG ATC CGG GCC ATA CAG GAC ACG AAG CTC CCG-3';

and

5-CCT AGG ATC CCC CTC ATA CCG GGG GGA GAG CAC ATT CAC-3'.

The ICAM-1 PCR products were digested with the restriction enzymes Mlu I and BamHI and ligated into the Mlu I-BamHI-cut CD8-IgG1 vector (Damle N. K. et al. (1991) Proc. Natl. Acad. Sci. USA 88: 6403) resulting in the preparation of the ICAM-1.2 Rg, and the ICAM-1.5 Rg fusion proteins.

ICAM-2 cDNA sequences (Staunton D. E. et al. (1989) Nature 339: 61) encoding the extracellular domain of ICAM-2 were amplified by PCR from 100 ng of an Mlu I linearized human placenta cDNA library prepared in the expression vector CDM8 (Seed B. (1987) Nature 329: 840). One forward primer complementary to sequences located immediately upstream from sequence encoding the N-terminal signal sequence of the ICAM-2 protein with the sequence, 5'CGC GAA GCT TCT AGA GAG ATG TCC TCT TTC GGT-3' was used in conjunction with two different reverse primers complementary to sequences located at the junction of the extracellular and transmembrane domain of ICAM-2. The two reverse primers have the following sequences:

5'-CCG CGG ATC CGC TGT CCG ACA AGG CTC ATA-3' and

5'-CGC TCG AGG ATC CTG GCT GTC CGA CAC AGG CTC-3'.

PCR products prepared with these oligonucleotides were subcloned into either the CD8-IgG1 expression vector (Damle N. K. et al. (1991) Proc. Natl. Acad. Sci. USA 88: 6403) to prepare the ICAM-2 Rg or in place of the two most N-terminal Ig-like domains of CD31 (Newman P. J. et al. (1990) Science 247: 1219; Simmons D. L. et al (1990) J. Exp. Med. 171: 2147) in a CD31 Rg construct to obtain the ICAM-2:CD31 Rg fusion proteins, respectively. The constructions of CD7 Rg and ELAM-1 Rg have been described (Damle N. E. et al. (1991) Proc. Natl. Acad. Sci. USA. 88: 6403; Walz G. et al. (1990) Science 250: 1132).

The resulting constructs were individually transected into COS cells and the desired fusion proteins recovered and purified from the supernatant of the transected cells as described (Damle N. E. et al. (1991) Proc. Natl. Acad. Sci. USA. 88: 6403).

EXAMPLE 2

Monoclonal Antibodies

Hybridomas OKT3 (anti-CD3), OKT4 (anti-CD4), OKT8 (anti-CD8), OKM1 (anti-CD11b), 7G7/B6 (anti-CD25), L243 (anti-HLA-DR), and 63D3 (anti-monocyte) were obtained from American Type Culture Collection, Rockville, Md. Hybridoma secreting anti-ICAM-1 mAb 84H10 was provided by Dr. P. Mannoni, Istitut Paoli Calmettes, Marseille, France. Ascitic fluids containing the respective monoclonal antibody (mAb) from these hybridomas were generated in pristane-primed BALB/c mice. Mab 9.6 (anti-CD2), 10.2 (anti-CD5), G10-1 (anti-CD8), 60.1 (anti-CD11b), FC2 (anti-CD16), 60.3 (anti-CD18), 1F5 (anti-CD20), 9.3 (anti-CD28), and HB10a (anti-HLA-DR) were provided by Dr. J. A. Ledbetter (Bristol-Myers Squibb). Mab MHM23 (anti-CD18) and MHM24 (anti-CD11a) were provided by Dr. A. McMichael, Nuffield Foundation, Osford UK. Mab 4G7 (anti-CD19) was provided by Dr. E. G. Engleman, Stanford University School of Medicine, Stanford, Calif. Mab WT-31 (anti-TCR-1) was provided by Dr. W. Tax, University of Nijmegen, Nijmegen, The Netherland, as was also obtained from Becton Tickings Monoclonal Center, Mountain View, Calif. Anti-Tac (CD25/IL-2Rα) mAb was provided by Dr. T. A. Waldmann, NIH, Bethesda, Md. Anti-CD11a mAb 2503, Anti-CD11c mAb BU15 and anti-CD18 mAb BL5 were obtained from Amac, Inc., Westbrook, Me. Each of the above mAb is an IgG antibody. FITC-labelled or PE-labelled mAb directed against various lymphoid surface molecules were obtained from Amac, or Coulter Immunology, Hialeah, Fla.

Isolation of CD4+ T Cells

Peripheral blood mononuclear cells from healthy donors were separated by Ficoll-Hypaque density gradient centrifugation. Resting CD4+ T cells were isolated by rigorous immunomagnetic negative selection using Dynabeads M-450 (Dynal Inc., Great Neck, N.Y.) as described in (Damle N. E. et al. (1991) Proc. Natl. Acad. Sci. SA. 88: 6403; Horgan K. et al. (1991) *In Current Protocols in Immunology.* J. E. Coligan, A. M. Kruisbeek, D. H. Margulies, E. M. Shevach, and W. Strober. Editors. pp. 7.4.1–7.4.6). Negative selection was performed using a cocktail of mAb against HLA-DR (L243 or HB10a) on B cells, monocytes and activated T cells, 63D3 (monocytes), CD19 (4G7) or CD20 (1F5) on B cells, CD11b (OKM1 or 60.1) on monocytes and NK cells, CD16 (FC2) on NK cells, and CD8 (OKT8 or G10-1) on CD8$^+$ T cells. The purity of the isolated CD4$^+$ populations was >95% as assessed by direct or indirect immunofluorescence analysis using a fluorescence activated cell sorter (EPICS V, Coulter, Hialeah, Fla.). Isolated CD4$^+$ T cells were resuspended with 100 UI/ml penicillin, 100 μg/ml streptomycin, 2 mM L-glutaine, and 10% fetal bovine serum. These CD4$^+$ T cells were unable to proliferate in response to mitogenic concentrations of PHA (10 μg/ml) or soluble anti-CD3/TCR (100 ng/ml) in the absence of accessory cells.

EXAMPLE 3

Generation of AG-Primed CD4$^+$ T Cells

Freshly isolated resting mononuclear cells were stimulated with staphylococcal exotoxins SEA, SEB, SEE, or TSST-1 (Toxin Technology, Inc., Sarasota, Fla.) (1 μg/ml) for 7 days following which CD4$^+$ T cells were isolated and propagated in the presence of irradiated class II MHC$^+$ B cells, individual exotoxin (1 μg/ml), and IL-2 (50 U/ml). DRw6-primed CD4$^+$ T cells were generated from the mixed lymphocyte culture (MLC) stimulated by irradiated DRw6$^+$ B cell line ARENT and propagated using ARENT B cells and IL-2 as described in (Damle N. K. et al. 91990) Eur. J. Immunol. 20: 1995). Prior to studying their responses, viable CD4$^+$ T cells were isolated from their growth/maintenance cultures by Ficoll-Hypaque density gradient centrifugation, maintained for 12–16 hours in complete mediuin (CM) in the absence of any stimulus.

EXAMPLE 4

Proliferation Assays

Round-bottom microtiter plates (Corning) were precoated for 12–16 hours at 4° C. with a mixture (10 μg/ml each) of affinity-purified goat anti-mouse and anti-human IgG Fc antibodies (Tago, Burlingame, Calif.) (40 μl/well in sodium bicarbonate buffer, pH 9.6) after which additional protein-binding sites were blocked for 12–16 hours with 2% bovine serum albumin in RPMI 1640. ICAM-1 Rg or ICAM-2 Rg (human IgG Fc) and anti-TCR-1 (mouse IgG) mAb were immobilized in the above microtiter wells for 1 hr and the plates were washed twice with CM as described (Damle N. K. et al. (1991) Proc. Natl. Acad. Sci. USA 88: 6403). These plates "armed" with ICAM Rg and/or anti-TCR-1 were then used to stimulate CD4$^+$ T cells. Fifty thousand CD4$^+$ in 0.2 ml of CM were cultured in the above "armed" microtiter plates for 96 hr at 37° C. in a 5% $CO_2$ and 95% air atmosphere. Proliferative responses in these cultures were measured usually on day 4 by pulsing triplicate cultures with 1 μCi/well of $^3$H-TdR (6.7 Ci/mM, New England Nuclear, Boston, Mass.) 16 hr before harvesting of cells for the measurement of radiolabel into newly synthesized DNA. The results are expressed as cpm±SEM.

EXAMPLE 5

Production of Interluekin-2 and Analysis of Interleukin-2 Receptor Expression

Fifty thousand resting CD4$^+$ T cells were cultured in 96-well microtiter plates previously "armed" with ICAM-1 or ICAM-2 Rg (50 ng/well), anti-TCR-1 (50 ng/ml) or both as described above. Cell-free supernatants from these cultures were collected after 48 hr and assayed for the interleukin 2 (IL-2) activity using the IL-2-dependent T cell line CTL-L2 as described (Gillis S. et al. (1978) J. Immunol. 120: 2027). The IL-2 concentration of each sample was calculated by reference to recombinant IL-2 (Cetus Corporation, Emeryville, Calif.) and expressed in international U/ml. For the analysis of CD25 (IL-2Rα)$^+$ CD4$^+$ T cells, cultures were harvested after 48–60 hr, stained with fluorescein-conjugated anti-CD25 mAb (Amac) and analyzed on a flow cytometer (EPICS, Coulter) as described (Damle N. K. (1991) Proc. Natl. Acad. Sci. USA 88: 6403).

EXAMPLE 6

Preparation of ICAM-1 and ICAM-2 Immunoglobulin Fusion Proteins

ICAM-1 and ICAM-2 Ig fusion proteins (receptor globulins, Rg) were prepared by fusion of a cDNA fragment encoding either a part of, or the entire extracellular region of these molecules to a genomic DNA fragment encoding the constant region of the human IgG1. Three ICAM-1 Rg chimeras were used in this study: ICAM-1.2 Rg, ICAM-1.4 Rg, and ICAM-1.5 Rg. These were derived from cDNA fragments encoding either the 2 or the 4 most N-terminal Ig-like extracellular domains of ICAM-1, or the complete extracellular domain of ICAM-1, respectively (FIG. 1). Two ICAM-2 fusion proteins were prepared for this study: 1) ICAM-2 Rg which contains a cDNA fragment encoding the complete extracellular domain of ICAM-2 fused to the genomic DNA fragment encoding the human IgG1 constant region, and 2) ICAM-2:CD31 Rg in which the cDNA fragment encoding the 2 most N-terminal Ig-like domains of a CD31 (PECAM) Rg fusion gene was replaced by a cDNA fragment encoding the two Ig like domains of ICAM-2 to obtain the ICAM-2:CD31 chimera (FIG. 1). Similarly prepared CD7 Rg and ELAM-1 Rg (Damle N. E. et al. (1991) Proc. Natl. Acad. Sci. USA. 88: 6403; Walz G. et al. (1990) Science 250: 1132) were also used in this study as controls.

The ability of ICAM-1 to costimulate T cell proliferation has been demonstrated (14). In preliminary studies, we confirmed the costimulatory effects of ICAM-1 Rgs and further compared the relative strengths of ICAM-1 Rgs bearing various N-terminal Ig-like domains. Both ICAM-1.4 Rg and ICAM-1.5 Rg were found to be equally costimulatory in T cell activation assays. Hence, in all subsequent experiments unless specified otherwise ICAM-1.4 Rg was used as ICAM-1.

EXAMPLE 7

Costimulatory Effects of ICAM-2

Figure 2:
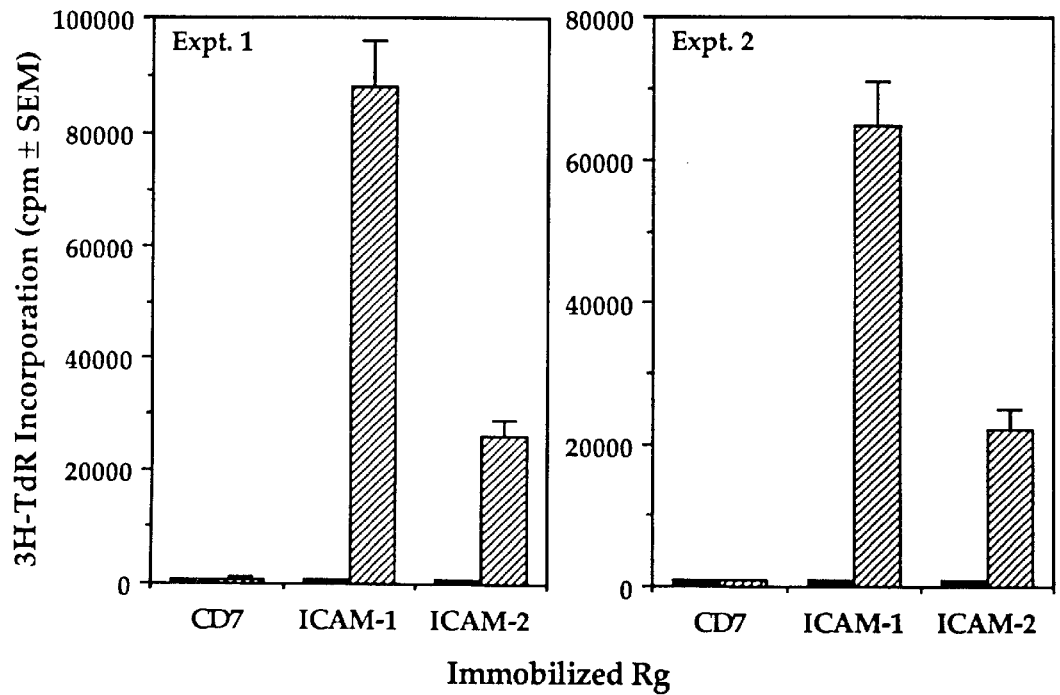
FIG. 2 illustrates the ability of CD7, ICAM-1 or ICAM-2 Rgs co-immobilized with anti-TCR-1 to stimulate proliferation of CD4$^+$ T cells. Fifty thousand resting CD4$^+$ T cells were cultured with immobilized CD7 Rg, ICAM-1.5 Rg, or ICAM-2 Rg (100 ng/well) and either anti-CD19 or anti-TCR-1 mAb (50 ng/well) in a final volume of 0.2 ml of complete medium per microtiter. 3H-TdR incorporation in these cultures was measured on day 4.

The ability of ICAM-2 Rg to provide costimulatory signals to CD4$^+$ T cells activated via the TCR complex was examined and compared with that of ICAM-1 Rg. ICAM-1 Rg or ICAM-2 Rg were co-immobilized (100 ng/well) with anti-TCR-1 mAb (50 ng/well) in microtiter wells and freshly isolated CD4$^+$ T cells were then added to these wells. Proliferative response of these T cells was monitored on day 4 as described in EXAMPLE 4. FIG. 2 shows that both ICAM-1 Rg and ICAM-2 Rg, when individually co-immobilized with anti-TCR-1 mAb, induced proliferation of CD4$^+$ T cells. In contrast, co-immobilization of anti-TCR-1 mAb and either ICAM Rgs must be co-immobilized in order to support T cell activation as neither ICAM-1 Rg nor ICAM-2 Rg in solution supported T cell proliferation in conjunction with immobilized anti-TCR-1 mAb. Additionally, mAb directed at T cell surface molecules CD2, CD5 or CD28 when co-immobilized with either ICAM Rg failed to stimulate T cells.

Figure 3:
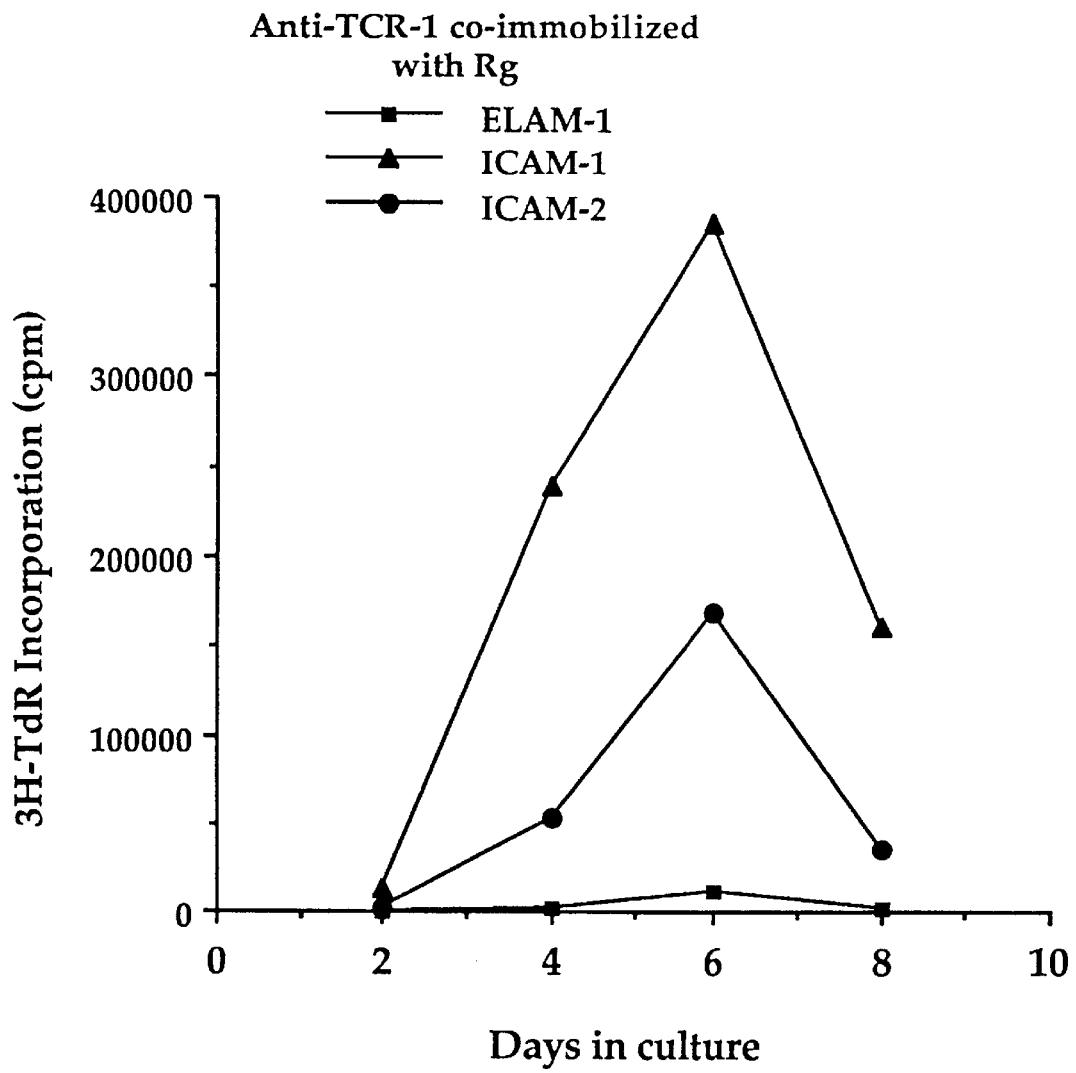
FIG. 3 illustrates the kinetics of the costimulatory effect of ICAM-1 and ICAM-2 Rg. Fifty thousand resting CD4+ T cells were cultured with anti-TCR-1 mAb (50 ng/well) co-immobilized with 100 ng/well of ELAM-1 Rg (as a control), ICAM-1 Rg or ICAM-2 Rg. Proliferative responses in these cultures were measured at indicated time points.

When co-immobilized with anti-TCR-1 mAb, the proliferative response induced by ICAM-1 Rg was consistently stronger than that induced by ICAM-2 Rg. The quantitative difference between CD4$^+$ T cell proliferation induced with ICAM-1 Rg and ICAM-2 Rg might have been due to differences in kinetics of these responses. The kinetics of costimulation of immobilized ICAM-1 Rg and ICAM-2 Rg were thus examined. As shown in FIG. 3, although both ICAM-1-induced and ICAM-2-induced proliferative responses of CD4$^+$ T cells were readily detected 4 days after the initiation of culture, the peak response with either ICAM was always observed on day 6 of culture. Extending culture period beyond 6 days usually resulted in reduced proliferation of T cells.

The concentration dependence of the costimulatory effects of ICAM-2 Rg and that of ICAM-1 Rg with either 4 (ICAM-1.4 Rg) or 2 (ICAM-1.2 Rg) N-terminal Ig-like domains was examined. As shown in FIG. 4, when co-immobilized with anti-TCR-1 mAb (50 ng/well) increasing concentrations of each ICAM Rg (5–500 ng/well) induced proportionately increased proliferative response by CD4$^+$ T cells. The observed difference between the relative costimulatory strengths of ICAM-1 Rgs and ICAM-2 Rg was apparent at each concentration tested. Both ICAM-1.2 Rg and ICAM-1.4 Rg induced quantitatively similar T cell proliferative responses. In contract, ICAM-2 Rg always induced weaker proliferative response of CD4$^+$ T cells than its ICAM-1 counterparts.

Figure 5:
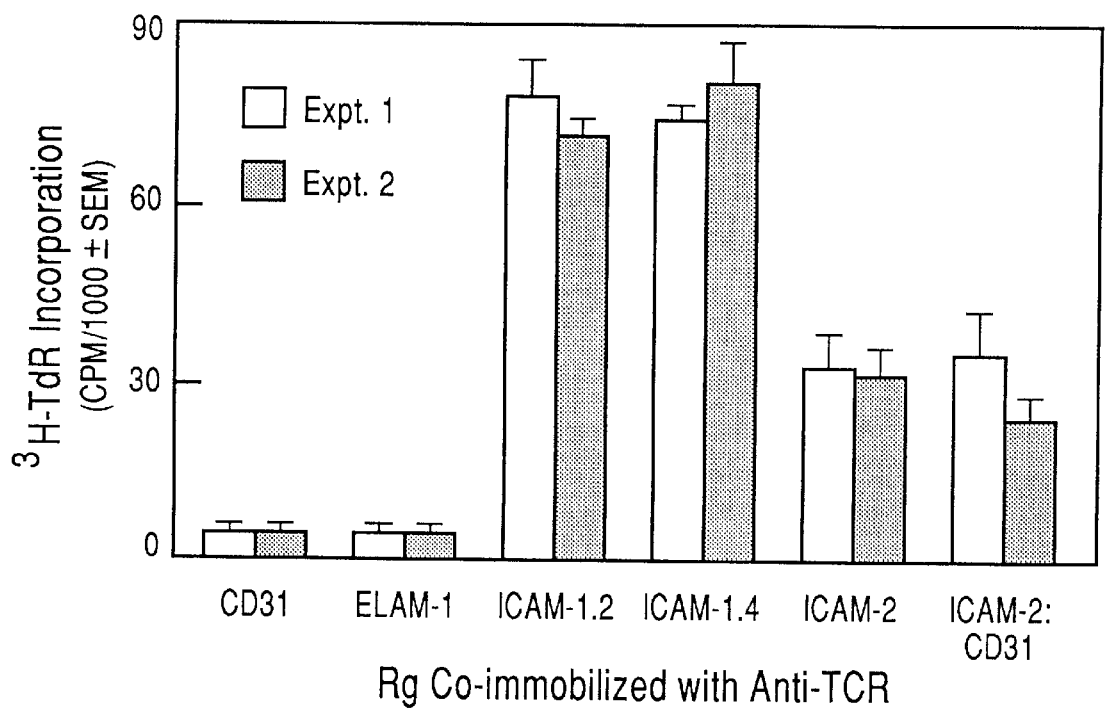
FIG. 5 illustrates the comparison of costimulatory activities of various ICAM Rgs. Anti-TCR-1 mAb (50 ng/well) was co-immobilized with 100 ng/well of CD7 Rg, CD31, ELAM-1, ICAM-1.2, ICAM-1.4, ICAM-2, or ICAM-2:CD31 Rgs prior to the addition of fifty thousand resting CD4+ T cells/well. Proliferative responses in these cultures were measured on day 4.

The relative abilities of ICAM-2 Rg and ICAM-2:CD31 Rg to costimulate CD4$^+$ T cells were examined. ICAM-2:CD31 chimera with 7 Ig-like domains was constructed by replacing two of the seven most N-terminal domains of CD31 Rg with the two domains of ICAM-2 as shown in FIG. 1. Both ICAM-2 Rg and ICAM-2:CD31 Rg induced quantitatively similar proliferative responses of CD4$^+$ T cells as shown in FIG. 5. The increase in the size of the ICAM-2 molecule with CD31-derived domains did not enhance the costimulatory property of ICAM-2. Both ICAM-1.2 Rg and ICAM-1.4 Rg were still more efficient than either ICAM-2 Rg or ICAM-2:CD31 Rg in inducing proliferation of CD4$^+$ T cells. Either CD31 Rg or ELAM-1 Rg (both used as negative controls) lacked the ability to co-stimulated CD4$^+$ T cells in conjunction with anti-TCR mAb.

EXAMPLE 8

Costimulatory Effect of ICAM-2 Rg on Antigen-Primed T Cells

Figure 6:
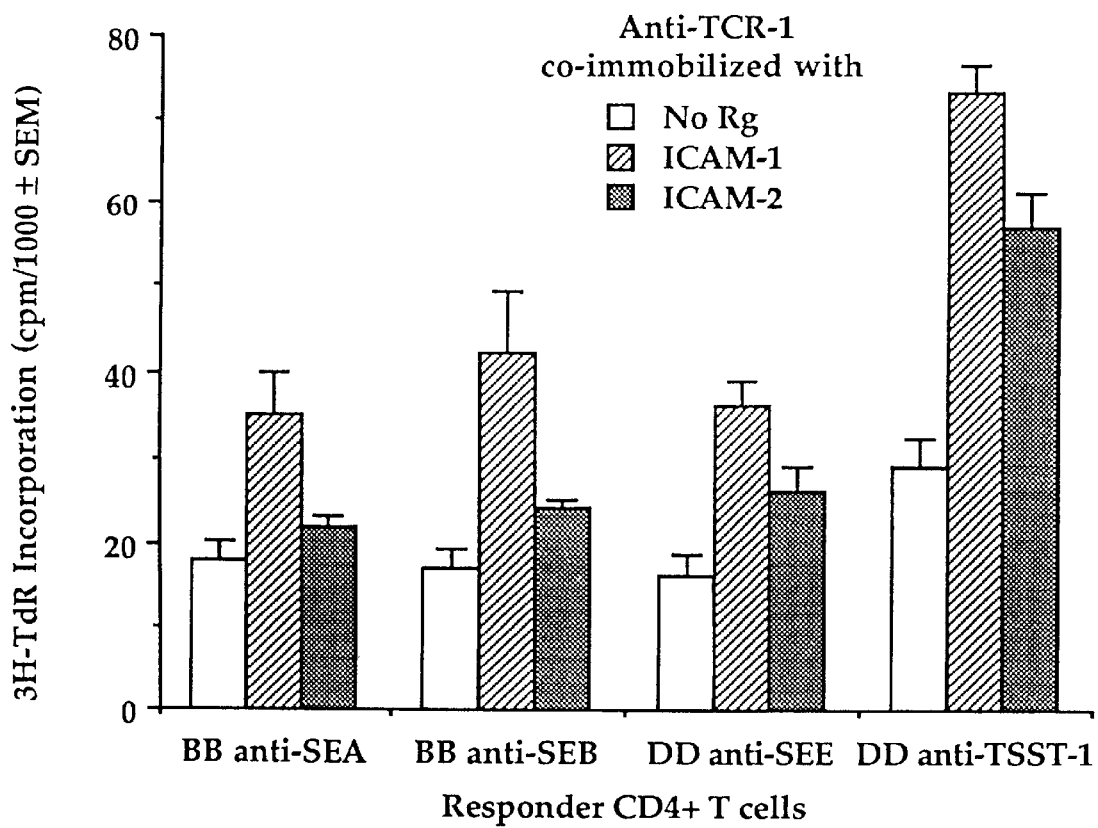
FIG. 6 illustrates that ICAM-2 Rg can also costimulate proliferation of Ag-activated CD4+ T cells. Anti-TCR-1 mAb at 50 ng/well was co-immobilized with or without 100 ng/well of either ICAM-1.4 Rg or ICAM-2 Rg in microtiter culture wells. Fifty thousand rested CD4+ T cells, either derived from cultures stimulated with distinct staphylococcal exotoxins, were added to these culture wells and their proliferative responses were measured on day 3.

The ability of ICAM-2 Rg to costimulate CD4$^+$ T cells which had been activated with antigen was examined. CD4$^+$ T cells isolated from cultures stimulated with staphylococcal exotoxins (super Ag) were rested for 12–16 hours in complete medium and then examined for proliferation in response to anti-TCR-1 mAb co-immobilized with ICAM-1 or ICAM-2 Rg. As shown in FIG. 6, immobilized anti-TCR-1 alone induced proliferation of Ag-primed CD4$^+$ T cells. However, co-immobilization of anti-TCR-1 with either ICAM Rg further increased this proliferation. The superior costimulatory effect of ICAM-1 Rg was also evident with Ag-primed T cells. Similar results were obtained using DRw6-primed CD4$^+$ T cell lines.

EXAMPLE 9

Figure 7:
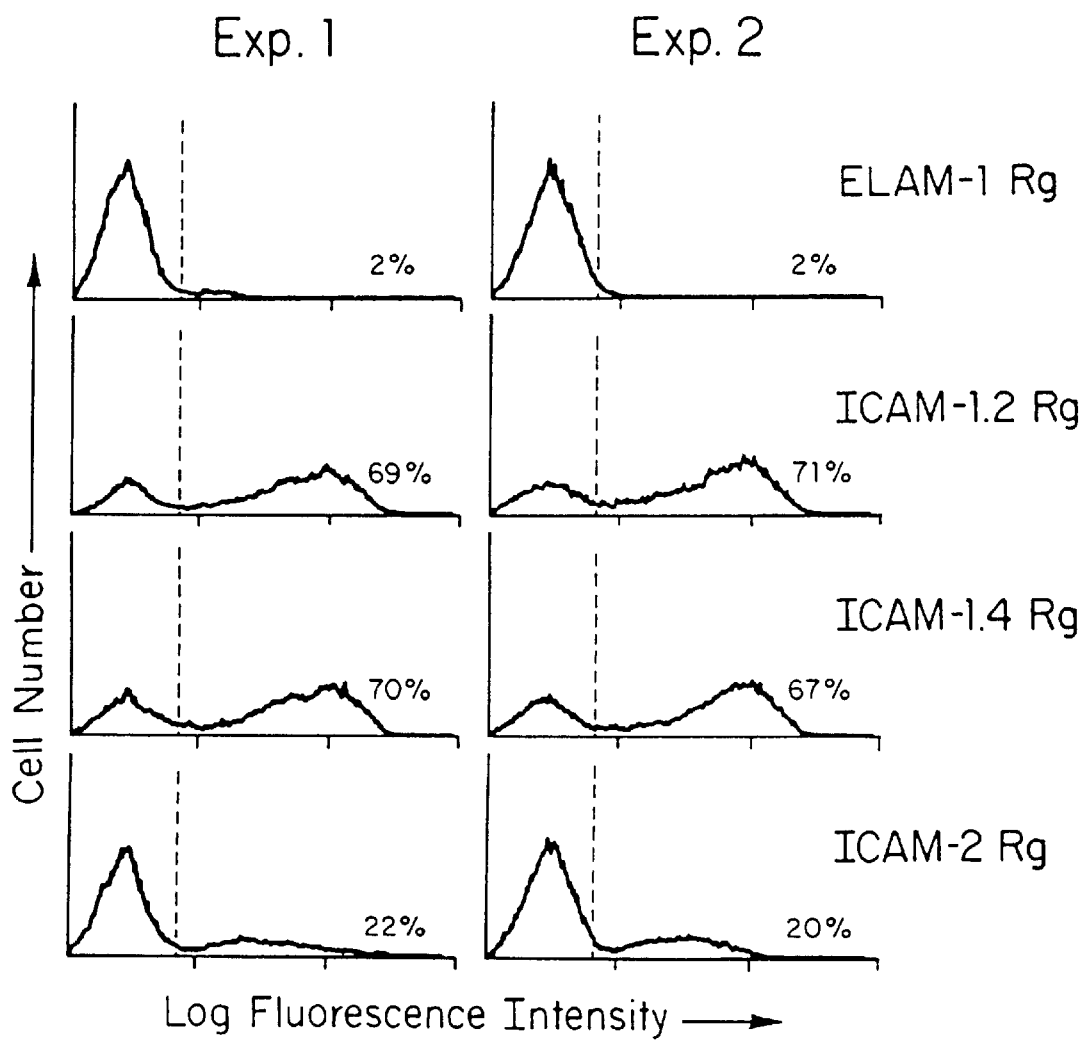
FIG. 7 illustrates the induction of CD25/IL-2Rα on the surface of CD4+ T cells by costimulation with ICAM Rgs. Resting CD25-CD4+ T cells were cultured with anti-TCR-1 (50 ng/well) co-immobilized with ELAM-1 (used as a control), ICAM-1.2, ICAM-1.4, or ICAM-2 Rgs (100 ng/well). After 60 hr, T cells were harvested from these cultures and examined for their expression of CD25 by direct immunofluorescence analysis.

Costimulatory Effect of ICAM-1 Rg and ICAM-2 Rg Involves the IL2/IL-2 Receptor System The ability of co-immobilized ICAM-2 Rg and anti-TCR-1 mAb to induce the expression of IL-2 receptors by CD4$^+$ T cells was examined. T cells were cultured in the presence of immobilized ICAM-2 Rg or anti-TCR-1 mAb or both and 60 hr later their levels of cell surface expression of CD25 (IL-2Ra) were monitored by flow cytometry. As shown in FIG. 7 binding of CD4$^+$ T cells to co-immobilized ICAM-1 Rg or ICAM-2 Rg and anti-TCR-1 mAb induced the expression of IL-2R on a significantly higher percent of CD4$^+$ T cells than those cultured with immobilized anti-TCR-1 mAb and EAM-1 Rg (>5% CD25$^+$) was always greater than that induced with co-immobilized ICAM-2 Rg (~25% CD25$^+$). In addition, CD4$^+$ T cells stimulated with anti-TCR-1 mAb and either ICAM-1 Rg or ICAM-2 Rg produced significantly more IL-2 (2.5–6 U/ml with ICAM-1 Rg and 1 U/ml with ICAM-2 Rg) than those which had been incubated in wells with immobilized anti-TCR-1 mAb alone or either of the immobilized ICAM Rgs (>0.1 U/ml). Thus, the difference in the relative costimulatory strengths of ICAM-1 and ICAM-2 Rgs was also apparent in their ability to induce IL-2R. Th mAb anti-Tac (anti-CD25) significantly inhibited the proliferative response of CD4$^+$ T cells induced by co-immobilization of anti-TCR-1 mAb and either ICAM-1 Rg or ICAM-2 Rg. Together these results show that the proliferative responses of CD4$^+$ T cells induced by co-immobilized anti-TCR-1 mAb and either of the ICAM Rgs is at least in part mediated via the IL-2/IL-2R autocrine system.

EXAMPLE 10

Role of CD11A/CD18 (LFA-1) During Costimulation with ICAM Rg

Figure 8:
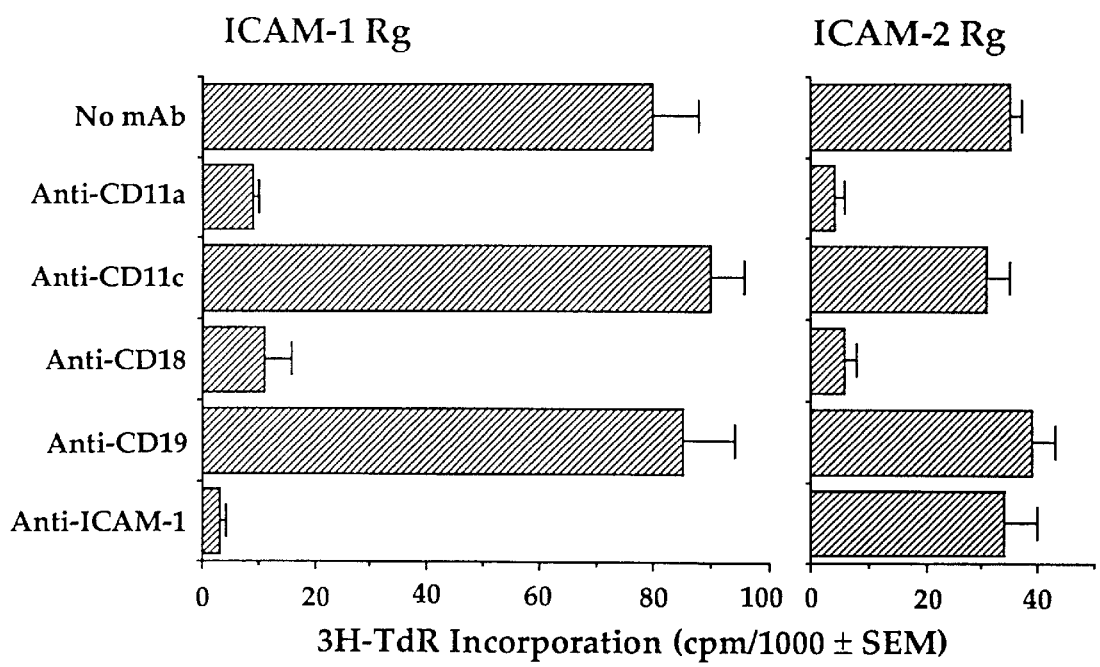
FIG. 8 illustrates that the costimulatory effect of ICAM-2 involves participation of CD11a/CD18 (LFA-1) complex on T cells. Fifty thousand CD4+ T cells were cultured with anti-TCR-1 co-immobilized with ICAM-1.4 or ICAM-2 Rg in the presence of soluble mAb (10 μg/ml) reactive with CD11a, CD11a, CD18, CD19, or ICAM-1. Proliferative responses in these cultures were measured on day 4.

Both ICAM-1 and ICAM-2 have been shown to bind CD11a/CD18 (LFA-1) on the surface of all leukocytes. The role of LFA-1 on the surface of T cells during the costimulatory effects of ICAM-1 and ICAM-2 was examined. Both ICAM-1 and ICAM-2 were independently co-immobilized with anti-TCR-1 mAb in microtiter culture wells. CD4$^+$ T cells were cultured in these wells in the presence of soluble mAb (10 $\mu$g/ml) directed at CD11a, CD11c, CD18, CD19, or ICAM-1. Mab directed at either CD11a or CD18 almost completely inhibited the proliferation of T cells induced with either ICAM in these cultures (FIG. 8). In contrast, the anti-ICAM-1 mAb 84H10 inhibited the responses of T cells to immobilized ICAM-1 Rg but not ICAM-2 Rg. The anti-CD19 mAb 4G7 used as a control did not inhibit the costimulatory effects of either ICAM Rg. These results demonstrate that the interactions of ICAMS with CD11a/CD18 (LFA-1) complex on the surface of T cells are critical to mediate the above mentioned costimulatory effects.

The foregoing description and Examples are intended as illustrative of the present invention, but not as limiting. Numerous variations and modifications may be effected without departing from the true spirit and scope of the present invention.

We claim:

1. A soluble fusion molecule comprising a first region, having the binding specificity for CD11a/CD18 of ICAM-2, operatively linked to a second region corresponding to an immunoglobulin constant region.

2. The fusion molecule according to claim 1, wherein the first region contains an extracellular portion of ICAM-2.

3. The fusion molecule according to claim 1, wherein the second region corresponds to an IgG constant region.

4. The fusion molecule according to claim 1 produced by recombinant expression.

5. The fusion molecule of claim 1, comprising a first region containing an extracellular portion of ICAM-2, operatively linked to a second region corresponding to an IgG constant region.

6. A recombinant fusion molecule comprising a first region, having the binding specificity for CD11a/CD18 of ICAM-2, operatively linked to a second region corresponding to an immunoglobulin constant region.

7. The recombinant fusion molecule according to claim 6, wherein the first region contains an extracellular portion of ICAM-2 and the second region corresponds to an IgG constant region.

8. The recombinant fusion molecule according to claim 7, wherein the fusion molecule is produced by:
   (a) subcloning a cDNA encoding an extracellular portion of ICAM-2 into an IgG expression vector, and
   (b) expressing and isolating recombinant fusion molecule containing an extracellular portion of ICAM-2 operatively linked to an IgG constant region.

9. A method of activating T cells comprising contacting T cells with a ligand capable of binding to CD3 on said T cells and an effective costimulatory amount of a soluble fusion molecule to activate the T cells, said soluble fusion molecule comprising a first region, having the binding specificity for CD11a/CD18 of ICAM-2, operatively linked to a second region corresponding to an immunoglobulin constant region.

10. The method according to claim 9, wherein the fusion molecule has a first region corresponding to an extracellular portion of ICAM-2 and a second region corresponding to an IgG constant region.

11. The method according to claim 9, wherein said fusion molecule is produced by recombinant expression.

12. A method of increasing the proliferative response of $CD4^+$ T cell comprising contacting said T cells with a ligand capable of binding to CD3 on said T cells, and a costimulatory soluble fusion molecule comprising a first region, having the binding specificity for CD11a/CD18 of ICAM-2, operatively linked to a second region corresponding to an immunoglobulin constant region.

13. The method of claim 12 wherein the fusion molecule has a first region corresponding to an extracellular portion of ICAM-2 and a second region corresponding to an IgG constant region.

14. The method according to claim 12, wherein said fusion molecule is produced by recombinant expression.

15. A method for inducing the production of IL-2 by T cells comprising contacting T cells with a ligand capable of binding to CD3 on said T cells and a costimulatory soluble fusion molecule comprising a first region, having the binding specificity for CD11a/CD18 of ICAM-2 operatively linked to a second region corresponding to an immunoglobulin constant region for a time period sufficient to induce IL-2 production by said T cells.

16. The method according to claim 15, wherein the fusion molecule has a first region corresponding to an extracellular portion of ICAM-2 and a second region corresponding to an IgG constant region.

17. The method according to claim 15, wherein said fusion molecule is produced by recombinant means.

\* \* \* \* \*